United States Patent
Francaviglia et al.

(10) Patent No.: US 10,478,522 B2
(45) Date of Patent: Nov. 19, 2019

(54) BIOCOMPATIBLE MATERIAL IN GRANULES MADE OF METAL MATERIAL OR METAL ALLOYS AND USE OF SAID GRANULES FOR VERTEBROPLASTY

(71) Applicant: MT ORTHO S.r.l., Aci Sant'antonio (IT)

(72) Inventors: Natale Francaviglia, Caltanissetta (IT); Gaetano Sorano, Trecastagni (IT); Roberto Drago, Viagrande (IT)

(73) Assignee: MT ORTHO S.R.L., Aci Sant'Antonio (IT)

( * ) Notice: Subject to any disclaimer, the term of this patent is extended or adjusted under 35 U.S.C. 154(b) by 295 days.

(21) Appl. No.: 15/327,248

(22) PCT Filed: Jul. 17, 2015

(86) PCT No.: PCT/IB2015/055437
§ 371 (c)(1),
(2) Date: Jan. 18, 2017

(87) PCT Pub. No.: WO2016/009406
PCT Pub. Date: Jan. 21, 2016

(65) Prior Publication Data
US 2017/0157287 A1    Jun. 8, 2017

(30) Foreign Application Priority Data
Jul. 18, 2014   (IT) .......................... MI2014A001318

(51) Int. Cl.
*A61L 27/06*     (2006.01)
*A61L 27/56*     (2006.01)
(Continued)

(52) U.S. Cl.
CPC ............... *A61L 27/06* (2013.01); *A61L 27/56* (2013.01); *B01J 19/085* (2013.01); *B01J 19/121* (2013.01);
(Continued)

(58) Field of Classification Search
CPC ........ A61L 27/06; A61L 27/56; B01J 19/085; B01J 19/121
See application file for complete search history.

(56) References Cited

U.S. PATENT DOCUMENTS 6,949,251 B2 * 9/2005 Dalal .................. A61L 27/12
                                                        424/423
7,357,941 B2 * 4/2008 Dalal .................. A61L 27/12
                                                        424/423
(Continued)

FOREIGN PATENT DOCUMENTS

DE    202013006283 U1    4/2014
WO    2009061251 A1      5/2009

OTHER PUBLICATIONS

Zimmer, Inc., Product information for Cancellous-structured Titanium (TM) (CSTi(TM)) 1-8 (2003).
(Continued)

*Primary Examiner* — Cam N. Nguyen
(74) *Attorney, Agent, or Firm* — Pepper Hamilton LLP

(57) ABSTRACT

More specifically, granules made of biocompatible metal material, preferably osteoinductive metal, for use in vertebroplasty surgery, as well as the use of these granules for this purpose, are the object of the present invention.

13 Claims, 3 Drawing Sheets

(51) Int. Cl.
*B01J 19/08* (2006.01)
*B01J 19/12* (2006.01)
*C22C 14/00* (2006.01)

(52) U.S. Cl.
CPC ....... *A61L 2400/18* (2013.01); *A61L 2430/38* (2013.01); *B01J 2219/0879* (2013.01); *B01J 2219/12* (2013.01); *C22C 14/00* (2013.01)

(56) References Cited

U.S. PATENT DOCUMENTS

| | | | | |
|---|---|---|---|---|
| 7,390,498 | B2* | 6/2008 | Dalal | A61L 27/12 |
| | | | | 424/423 |
| 8,173,149 | B2* | 5/2012 | Dalal | A61L 27/12 |
| | | | | 424/423 |
| 8,821,586 | B2* | 9/2014 | Bjursten | A61F 2/28 |
| | | | | 623/11.11 |

OTHER PUBLICATIONS

PCT International Search Report and Written Opinion corresponding to PCT/IB2015/055437, filed Jul. 17, 2015 (dated Oct. 19, 2015).

\* cited by examiner

BIOCOMPATIBLE MATERIAL IN GRANULES MADE OF METAL MATERIAL OR METAL ALLOYS AND USE OF SAID GRANULES FOR VERTEBROPLASTY

This application is a national stage application under 35 U.S.C. § 371 of PCT Application No. PCT/IB2015/055437, filed Jul. 17, 2015, which claims the priority benefit of Italy Patent Application No. MI2014A001318, filed Jul. 18, 2014, which is hereby incorporated by reference in its entirety.

FIELD OF THE INVENTION

The present invention concerns transcutaneous vertebroplasty or kyphoplasty surgery.

More specifically, granules made of biocompatible metal material, preferably osteoinductive metal, to be used in vertebroplasty, and also the use of these granules for this purpose, are the object of the present invention.

BACKGROUND OF THE INVENTION

Vertebroplasty, or kyphoplasty, is a treatment used in patients with vertebral compression fractures.

Many causes can determine the collapse of a vertebra under the action of the compressive forces that normally affect the spinal column: painful compression fractures from osteoporotic, traumatic or osteolytic compression of the thoracic or lumbar vertebrae can occur. The main causes are osteoporosis, multiple myeloma, vertebral metastases, or more simply a trauma.

As is known (see accompanying FIGS. 1 and 2), the vertebrae 10 have a main body 11 of a substantially cylindrical shape (or better, slightly "hourglass" shape), in which a peripheral ring of cortical bone and a central portion of cancellous bone 12 and a plurality of processes (superior articular, inferior articular, transverse and spinous) that extend posteriorly 13 are identifiable.

80% of the load is borne by the main body 11, while the pedicles and the processes 13 perform a dynamic function and are allocated to bear only a small portion of the load.

Compression fractures therefore substantially concern the main body.

As mentioned, the fracture can originate due to an osteoporosis situation affecting the cancellous bone, which, due to the compromised trabecular structure, no longer exerts its support function and collapses under the action of compression loads. A collapse of the cancellous bone then involves the occurrence of fractures even in the cortical bone.

Surgical methods are known in the prior art that are aimed at restoring the load-bearing capacity of the vertebra by means of the insertion of prosthetic aids such as flexible rods, screws and nails.

These surgeries, as can also be understood by those not skilled in the art, are very invasive both due to the fact that they require the surgeon to create a large access means, and due to the fact that the application of rods, screws and nails is in any case an surgery that is heavy for the patient's body and burdensome from the point of view of the body's full adaptation in the presence of the prosthesis.

A mini-invasive surgical technique has been more recently developed and established that requires both a much more contained access means, of a few millimeters, and reduced stress for the patient's body, even in the post-surgical period.

This technique is known as kyphoplasty or vertebroplasty, and is performed by inserting a balloon catheter or a mechanical dilator made of polymer material into the vertebral body through a metal cannula of a greater size (about 5 mm in diameter).

The technique most used provides for the use of a balloon 30: the surgeon, after creating the necessary access means, inserts the cannula 20 into the collapsed vertebra, which allows the balloon 30 to be inserted into the main body 11 of the vertebra, in the area in which the collapsed cancellous bone 12 no longer performs its support function.

With the patient in the prone and distracted position, one proceeds with the insertion of the cannula directly into the main body of the vertebra, with transpedicular access. The entire surgical step takes place under fluoroscopy.

Once the correct position within the main body of the vertebra has been reached, a bone compression device, which is nothing more than a balloon that is inflated by means of liquid or equivalent systems, is inserted by means of the cannula. The balloon performs the function of compacting the trabeculae of the cancellous bone of the main body of the vertebra, while at the same time expanding the internal cavity of the collapsed vertebra.

Once the cavity of the vertebra has been expanded by means of the balloon, the latter is retracted and cement of common use in orthopaedics, namely PMMA (polymethylmethacrylate), is inserted into the cavity thus formed, always by means of a cannula.

The use of cement in kyphoplasty has the advantage of immediately ensuring primary stability, namely resistance to the compression loads that act on the column, which guarantees a very short hospitalisation for the patient, such that the patient himself can be discharged within a few days of surgery.

On the other hand, many drawbacks are associated with the use of PMMA in kyphoplasty.

A very first drawback connected to the use of cement is the development of heat generated by the polymerization reaction, which is highly exothermic. The increase in temperature (12-14 Kcal are produced per 100 g cement) homogeneously develops within the concrete mass to then be transmitted towards the surface where it is disposed of. Temperatures close to 80° C. are also reached. Such high polymerization temperatures can cause localised bone necrosis problems.

A further disadvantage arising from the use of cement consists of the fact that microscopic cement fragments can become detached and escape from the main body of the vertebra through the fractured cortical bone fractured. Cases in which cement particles have escaped from the vertebra causing thrombi or other extremely dangerous situations for the patient are not rare in literature.

Not least, a problem left unresolved by the kyphoplasty surgeries of the type described thus far and which use cement to restore the support function performed by the cancellous bone having trabecular structure, consists of the fact that the surgery does not treat the compromised bone, in particular it does not treat the fracture, but limits itself to replacing the compromised cancellous bone with a synthetic material that accomplishes the support function performed by the healthy bone.

SUMMARY

The main object of the present invention is therefore to overcome the drawbacks left unsolved by the currently used methodologies, and in particular to completely eliminate the drawbacks linked to the use of cement (PMMA) in kyphoplasty surgeries.

Within this object, one aim of the present invention is therefore that of eliminating the problems linked to the high-temperature polymerization of the PMMA.

A further aim of the present invention consists of completely eliminating the risk of microscopic particles of material escaping from the vertebral body and be transported into the body, with the well-known detrimental consequences reported in the clinical follow-up studies of kyphoplasty implants with cement.

It is again the aim of the present invention to provide a biocompatible material that can be used in kyphoplasty surgeries to replace the cement (PMMA) and that is also osteoinductive, i.e. able to stimulate and promote bone regeneration and osseointegration, so as to treat the compromised bone instead of replacing the bone with cement to restore the mechanical load-supporting function.

This object, and these and other aims that will become clearer below following a detailed description of the present invention given here by way of a non-limiting example, are achieved by a biocompatible material in granules, preferably based on metal alloys, according to the accompanying claims.

LIST OF DRAWINGS

Further characteristics and advantages of the present invention shall become clearer from the following detailed description, provided by way of a non-limiting example and illustrated in the accompanying drawings, wherein.

DETAILED DESCRIPTION

According to the present invention, granules made of biocompatible metal material, more particularly based on titanium and/or its alloys, are produced with characteristics such as to make the insertion of granules and osseointegration, once in place, simultaneously possible during the surgical phase.

The term "granules" is used in the present description to indicate solid particles having any geometry whatsoever, preferably, but not exclusively an approximately spherical geometry, and having average size of the order of a few millimeters, preferably less than 7 mm, even more preferably but not necessarily between 4 and 6 mm.

In the case in which these granules have a spherical geometry, they will be characterized by an outer diameter of a few millimeters, preferably less than 7 mm, more preferably but not necessarily between 4 and 6 mm.

According to a preferred embodiment of the present invention, said granules will have spherical shape, in particular they will have a solid spherical structure. According to a less preferred variant, said granules could have a hollow spherical shape.

Preferably, said spheres will have a porous outer surface.

Even more preferably, the surface of said spheres will have a trabeculated and perforated structure, so as to promote osseointegration.

Granules or spherical particles with solid or hollow and outer surface having a trabeculated structure according to the present invention were obtained by the applicant by means of production techniques that envisage the localised precision casting of powders (metal or polymeric) by means of high-energy electron beams. Nowadays, these techniques, known as EBM, acronym of the English expression Electron Beam Melting, are extremely avant-garde manufacturing technologies that allow objects having even very complex geometry and with different surface roughness to be produced starting from a computer drawing of the finished product, which is processed by computerised machines that guide the electron beam in its action.

Electron beam melting is a relatively new rapid prototyping technique for producing structures for implants, and allows complex three-dimensional geometries to be produced.

Using this technique, many surface characteristics can be designed so as to develop the superficially optimal structure for osseointegration, proliferation, and differentiation for non-cemented prostheses.

According to the present invention, this technology can be used to produce granules made of metal material or metal alloys, having a solid or hollow spherical structure, with trabeculated surface and surface roughness that allows and indeed promotes osseointegration and bone regeneration.

Preferably, the granules according to the present invention will have a surface having a regular trabecular structure, with pore size between one trabecula and the next of the order of a hundred or so microns.

Figure 1:
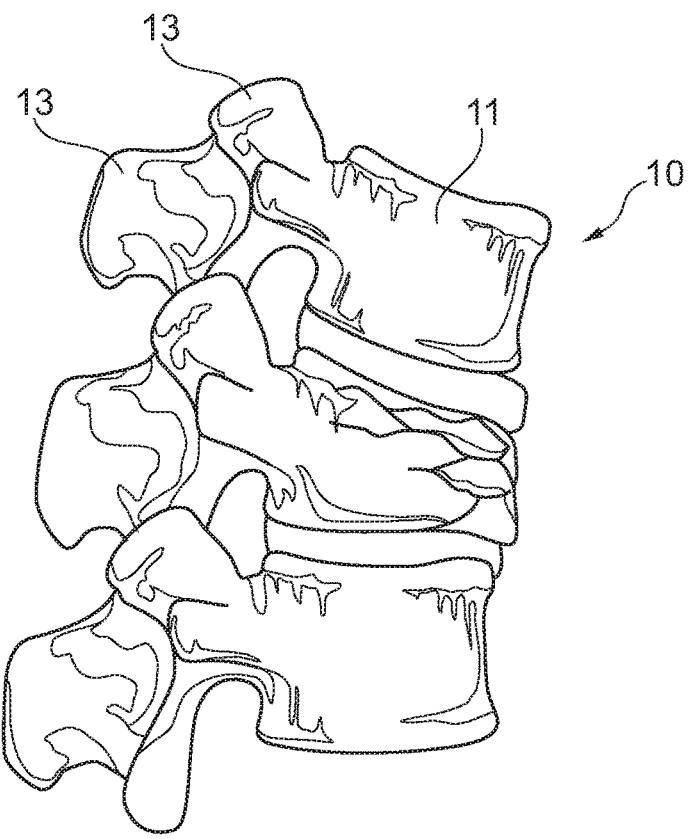
FIG. 1 shows a drawing representing a side view of a portion of vertebral column.
Figure 2:
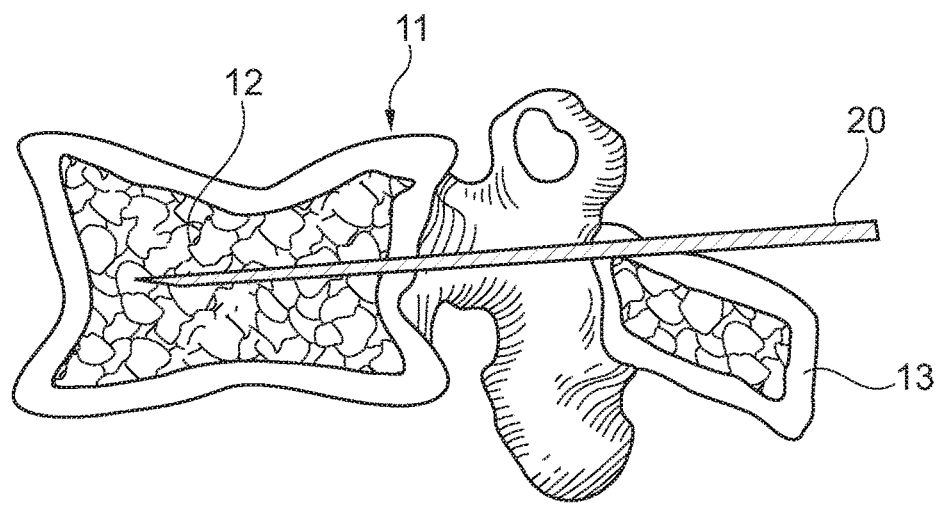
FIG. 2 shows a section of biconcave collapsed vertebra wherein the main body, the cancellous bone, and a cannula inserted into said main body with pedicular access are visible.
Figure 3:
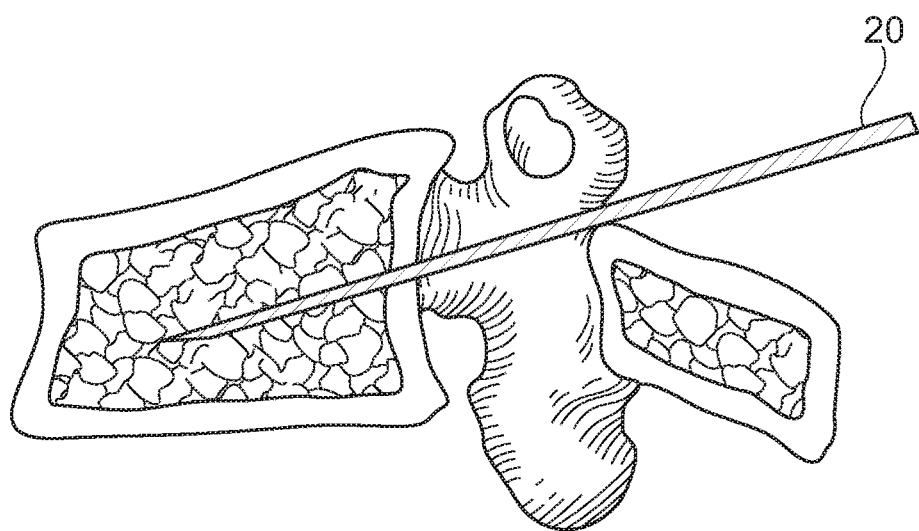
FIG. 3 shows a section of the collapsed vertebra with wedge-shape and with cannula inserted into the main body.
Figure 4:
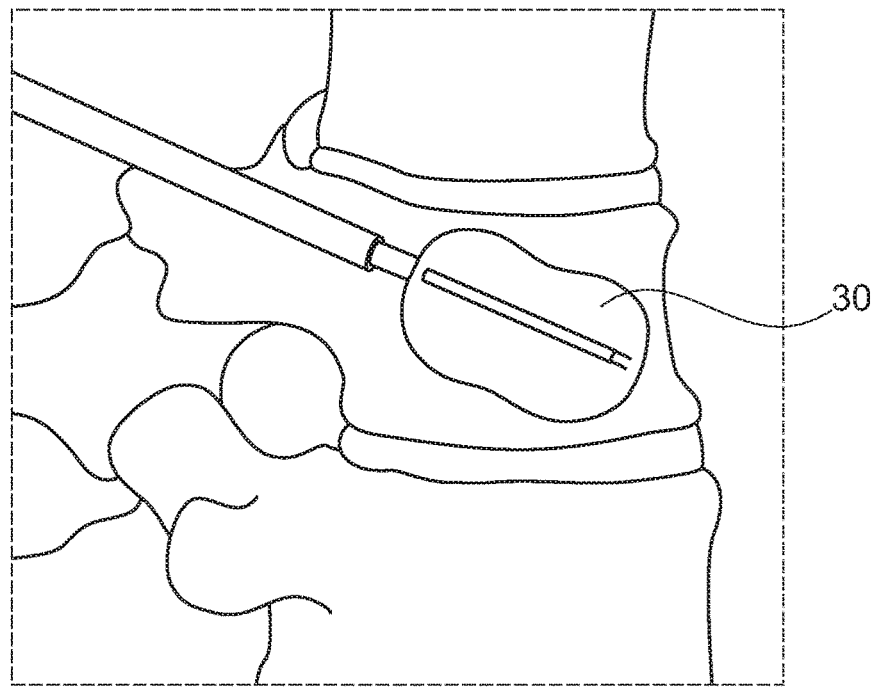
FIG. 4 shows the insertion of a known balloon into the main body of the vertebra.
Figure 5:
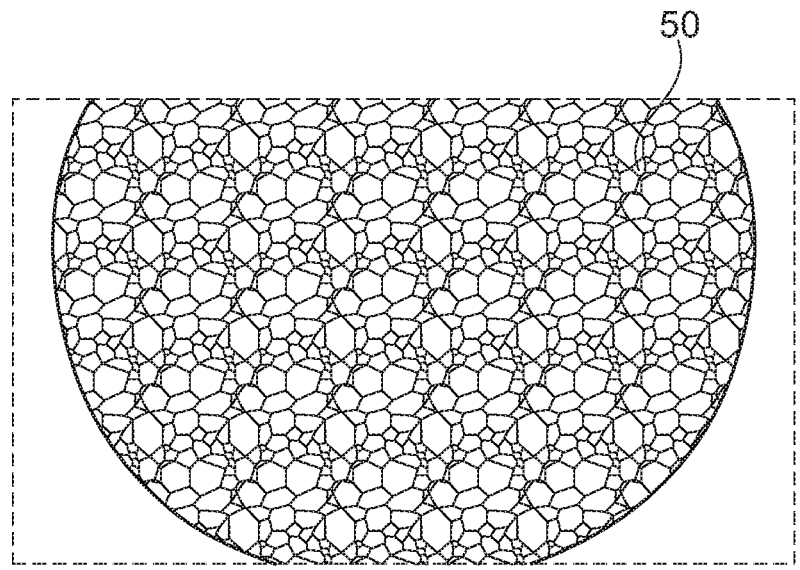
FIG. 5 shows a porous trabecular surface made of titanium or titanium alloy.

One example of titanium surface having a trabecular structure is shown in FIG. 5.

Figure 6:
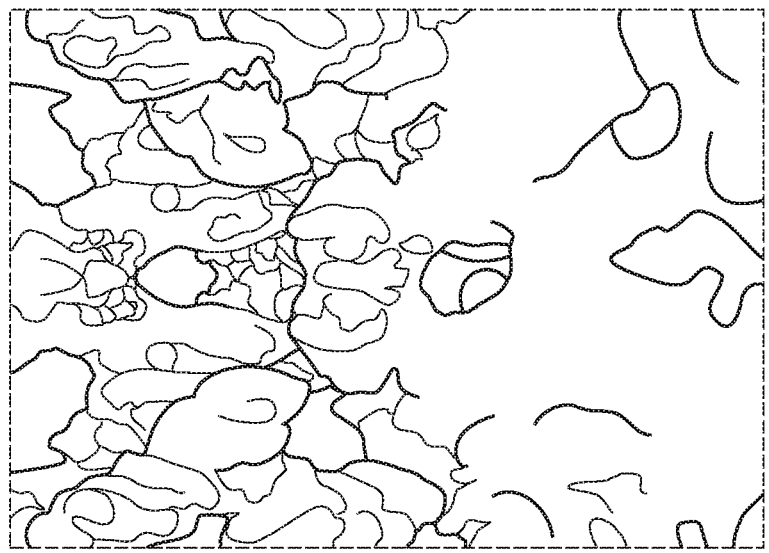
FIG. 6 shows an electron microscopic view of the structure of the trabecular bone.

FIG. 6 shows an electron microscopic view of the structure of the trabecular bone.

More specifically, the regular trabeculated structure will have pore diameter ranging between 300 and 1000 microns, more preferably between 400 and 800 microns, even more preferably the pore diameter will be of about 600 microns, preferably of 640 microns.

In particular, thanks to an elastic module very similar to that of the natural trabecular bone, the trabecular structure made of titanium or titanium alloys restores the physiological transfer of the loads, preventing damage to the bone and, indeed, promoting the regeneration thereof.

The trabecular titanium is able to stimulate osseointegration: in vitro studies demonstrate that within three weeks of implant there is already full colonisation of the trabecular structure on the part of the osteoblasts, while in vivo studies already show an excellent osseointegration at 26 weeks with new lamellar bone formations.

According to a preferred embodiment of the present invention, the granules of biocompatible material are made of a metal material, preferably titanium or its alloys, such as for example the titanium-aluminium-vanadium TiAl4V alloy, or pure grade 2 titanium or chrome-cobalt alloys or other materials having analogous characteristics in terms of biocompatibility and able to promote bone regeneration. As mentioned, kyphoplasty or vertebroplasty surgery provides for the use of a balloon or analogous system that allows the now compromised cancellous bone to be compacted and the internal cavity of the body of a vertebra to be expanded.

Even in the case of the use of granules according to the present invention instead of the cement in use in the state of the art, the surgical technique remains entirely unchanged.

Once the balloon, or other analogous device, has been retracted and the cavity of the vertebrae prepared, the surgeon will proceed with the insertion of the granules according to the present invention instead of the PMMA.

Inclusion of the granules according to the present invention can preferably take place via a cannula that is identical or altogether analogous to the one currently used in kyphoplasty surgeries with balloon and insertion of PMMA.

The granules of the present invention can therefore be deposited within the cavity of the main body of the vertebra with the same methods with which the cement is currently deposited with the system of the prior art.

The volume that must be filled by the granules is the same volume that is filled by the cement, it is a matter of just a few cc, more particularly of 1.5-2.0 cc.

According to what has been described, the granules according to the present invention have medium sizes of the order of millimeters, necessarily smaller than the diameter of the cannula by which means the granules are introduced into the cavity of the vertebrae, but in any case a limited number of granules will easily fill the available volume.

In order to facilitate insertion of the granules through the cannula, the use of a carrier substance, such as saline, serum, or other substance capable of assisting the sliding of the granules within the cannula by reducing the friction, may advantageously, but not necessarily be provided.

Again, the granules can advantageously be connected to each other to form a chain by means of connecting means adapted to restrict the relative mobility of the granules, one with respect to the others.

More particularly, according to a preferred embodiment of the present invention, the granules have a substantially spherical hollow shape and each sphere has a pair of slots located in diametrically opposite position, each of said slots being interconnected to a corresponding slot of an adjacent granule.

A veritable chain of spheroidal granules is produced in this way so as to restrict the relative mobility of the granules, one with respect to the other.

Thanks to this expedient, i.e. the presence of connecting means that restrict the relative mobility of the granules, the further advantage of compacting the granules within the cavity of the vertebrae, which is filled in an orderly fashion by the granules, is obtained. The fact of connecting the granules to each other allows greater control of the deposition process thereof within the vertebral cavity by the surgeon.

Once the granules have uniformly filled the vertebral cavity, the primary stability is guaranteed by the fact that the granules fill the cavity in a compact manner, homogenously transferring the loads.

Stability is then guaranteed by the osseointegration processes that the material the granules are made of and the trabeculated conformation of the surface are able to promote.

The titanium and its alloys, in particular, are known in literature as having properties that are biocompatible and able to promote regeneration of the trabecular bone, and thus healing of the compromised bone, a result that is impossible to achieve with an inert material such as the current PMMA.

The use of said granules in vertebroplasty or kyphoplasty surgeries is also the object of the present invention.

The invention claimed is:

1. A granule made of biocompatible metal material or alloys of said metal material, wherein said granule comprises a solid spherical structure with an outer diameter of between 3 and 4 millimeters, and an outer surface having a trabeculated porous structure, wherein the trabeculated pores of the outer surface have a diameter of between 400 and 800 microns.

2. The granule according to claim 1, wherein the pore diameter is about 600 microns.

3. The granule according to claim 1, wherein said granule is made of titanium or titanium alloys.

4. The granule according to claim 1, wherein said granule is made by means of production techniques that provide for at least one step of localized micro-fusion of powders through high energy electron beams (EBM) or laser.

5. The granule according to claim 1, wherein said granule has an average size of smaller than 7 mm.

6. The granule according to claim 1, wherein said granule comprises a connecting means for connecting said granule to at least another granule.

7. Two or more granules of claim 6 connected together to form a chain of granules.

8. The granule according to claim 1, wherein the pore diameter is 640 microns.

9. The granule according to claim 1, wherein said granule is between 1 and 6 mm in size.

10. The granule according to claim 1, wherein said granule is between 4 and 6 mm in size.

11. The granule according to claim 1, wherein said granule has an outer diameter of about 3 millimeters.

12. The granule according to claim 1, wherein said granule has an outer diameter of 3.3 millimeters.

13. A method of performing a vertebroplasty surgery, said method comprising:
   selecting a subject in need of vertebroplasty surgery;
   providing a composition comprising a plurality of the granules of claim 1; and
   depositing said composition into an internal cavity of one or more vertebra of the selected subject.

* * * * *